United States Patent [19]

Hasegawa et al.

[11] Patent Number: 5,364,626

[45] Date of Patent: Nov. 15, 1994

[54] REPELLING MATERIAL FOR ANIMALS

[75] Inventors: Masamitsu Hasegawa, Yawata; Yasuhisa Kuroda, Nara, both of Japan

[73] Assignee: Osaka Gas Company Ltd., Japan

[21] Appl. No.: 910,332

[22] PCT Filed: Nov. 29, 1991

[86] PCT No.: PCT/JP91/01655

§ 371 Date: Jul. 22, 1992

§ 102(e) Date: Jul. 22, 1992

[87] PCT Pub. No.: WO92/09196

PCT Pub. Date: Jun. 11, 1992

[30] Foreign Application Priority Data

Nov. 29, 1990 [JP] Japan .................... 2-128623

[51] Int. Cl.⁵ .................. A01N 25/34; A01N 25/26
[52] U.S. Cl. .................. 424/403; 424/402; 424/405; 424/408; 424/409; 424/411; 424/412; 424/413; 424/414; 424/415; 424/417; 424/421; 424/DIG. 10; 514/918; 514/919; 514/920; 428/905; 428/907; 428/224
[58] Field of Search ............ 424/411, 409, 402, 403, 424/405, 408, 413, 412, 414, 415, 417, 421, DIG. 10; 514/918, 919, 920, 876, 875; 428/905, 907, 224

[56] References Cited

U.S. PATENT DOCUMENTS 4,548,764 10/1985 Minteanu et al. .................. 424/9
5,023,082 6/1991 Friedman et al. .................. 424/485

FOREIGN PATENT DOCUMENTS 329868 8/1989 European Pat. Off. .
50-116638 9/1975 Japan .
61-194001 8/1986 Japan .
63-39533 2/1988 Japan .
01-110602 4/1989 Japan .
02-19305 1/1990 Japan .

OTHER PUBLICATIONS

Chemical Abstracts 83(7):54611g (1975).
Chemical Abstracts 78(3):12702d (1973).

Primary Examiner—Richard L. Raymond
Assistant Examiner—John D. Pak
Attorney, Agent, or Firm—Larson and Taylor

[57] ABSTRACT

A repelling material for animals retaining a great amount of a repellent and also having an excellent sustained release property can be obtained by adsorbing the repellent and at least one substance of phthalic acid esters, citric acid esters and glycols.

4 Claims, 4 Drawing Sheets

REPELLING MATERIAL FOR ANIMALS

TECHNOLOGICAL FIELD

The invention relates to a repelling material for animals prepared by adsorbing an repellent on active carbon fiber.

BACKGROUND ART

As a repellent preventing animals from approaching, cinnamic aldehyde, γ-nonylolactone, rosegeranium oil, sandalwood oil, menthol, citral, cinnamic alcohol, methyleugenol, geraniol, linalool and the like are known. In addition, limonene and the like are known as disclosed in Japanese Unexamined Patent Publication No. 110602/89.

As disclosed in the above-mentioned publication, said repellents were applied to an objective place in themselves or in the form of preparations with the addition of diluent, extending agent, retaining agent, excipient, emulsifier and the like by the following means:

(1) applying a repellent in a powder form.
(2) spraying a repellent in a liquid form.
(3) applying a repellent in a tablet form.
(4) filling a repellent in a capsule made of low air-permeable material such as gelatin, polyvinylalcohol, maltose and the like and puting the capsule at an objective place.
(5) adding a repellent in a bag made of polyethylene, polyvinylchloride, paper or the like and putting the bag at an objective place.
(6) putting a repellent in a film for bag-production by mixing a repellent into a melt of synthetic resin material.
(7) impregnating a repellent with paper and laminating one or two sides of the paper with a film made of polyethylene and like synthetic resin.

A conventional repelling material for animals produced by retaining a repellent (e.g. repelling material for animals, birds and the like) on a granulated active carbon has only a short life so that development of a repelling material for animals retaining more amount of a repellent, gradually releasing the repellent and having a long life is earnestly desired.

DISCLOSURE OF THE INVENTION

The inventors have conducted an extensive research on a repelling material for animals retaining more amount of a repellent, gradually releasing the repellent and having a long life, found that a repelling material for animals retaining more amount of a repellent, not rapidly releasing the retained repellent and having a long life can be produced by using special chemical substances as a sustained release agent, and accomplish the invention.

Thus, the present invention relates to "a repelling material for animals adsorbing at least one substance of phthalic acid esters, citric acid esters and glycols and an repellent on active carbon fiber".

As active carbon fibers, each fiber derived from pitch, polyacrylonitriles (PAN), phenols, celluloses and the like can be used.

The active carbon fiber is usually about 2 to about 3 μm in diameter of fiber, about 500 to about 2500 $m^2/g$ in specific surface area, about 10 to about 40 Å in diameter of pore, and distribution of pore size of the active carbon fiber is sharp.

As a repellent, a variety of chemical substances can be selected in accordance with a field of application.

In case of an animal repellent, the following chemical substances can be exemplified.

As repellents for dogs and cats, one or more of cinnamic aldehyde, γ-nonylolactone, lemon oil, paracresol acetate and the like can be used.

As repellents for pigeons, sparrows, bulbuls and like birds, one or more of phenylethylalcohol, geraniol, rosegeranium oil (a general term of benzylbenzoate, linalylacetate, linalool etc.), spearmint oil, L-carvone, bornylacetate, camphor, tetrahydrothiophene, citronellol and the like can be used.

As repellents for cockroaches, one or more of cinnamic alcohol, methyleugenol, geraniol and the like can be used.

As repellents for mosquitoes, one or more of sandalwood oil, menthol, citral and the like can be used.

However, a repelling material for animals has a short life by simply retaining the repellent only on a carrier due to rapid release of the repellent in a short time. The inventors conducted a further extensive research on a sustained release agent exerted an excellent sustained release effect and found that phthalic acid esters, citric acid esters or glycols exerted a desired effect. The chemical substances exerting a sustained release effect are exemplified such as: diethylphthalate, dibutylphthalate and the like being exemplified as esters of phthalic acid; triethylcitrate, trimethylcitrate and the like being exemplified as esters of citric acid; dipropylene glycol, butyldiglycol and the like being exemplified as glycols.

When not using a sustained release agent, active ingredients are rapidly released while repelling material for animals is allowed to stand in contact with air. When content of the sustained release agent is too much, the effect as repelling material for animals becomes decreased. Thus, the quantity of a sustained release agent used is preferably 1 to 9 parts by weight, more preferably 2.33 to 9 parts by weight per 1 part by weight of a repellent.

The active carbon fiber retaining an repellent in a variety of shapes, such as felt-like, a felt supported by polyester and like unwoven fabric in one or both sides, sheet-like, string-like, a component having a higher bulk density formed by dry or wet process can be used.

The present repelling material for animals can be produced by dipping active carbon fibers in a predetermined form with a mixed solution of a repellent and a sustained release agent, and impregnating and retaining a predetermined amount of the repellent and the sustained release agent. It can also be obtained by adding dropwise a mixed solution of a repellent and a sustained release agent to active carbon fibers. Further, it can be prepared by adsorbing a sustained release agent after adsorbing a repellent on active carbon fibers, or by adsorbing a repellent after adsorbing a sustained release agent on active carbon fiber. Further, it can be obtained by adsorbing a repellent and a sustained release agent on active carbon fiber alternately. In these producing methods, a method for adsorbing mixture of both substances is more preferable.

The repelling material for animals formed by impregnating an repellent and a sustained release agent is used in an air-permeable bag or a container having a venting hole or an opening. The repelling material for animals is sealed so as not to releasing an active ingredient when stored or carried. Diluent, extending agent, other sustained release agent not mentioned above, excipient, emulsifier and the like can be additionally used, if necessary.

BEST MODE OF CARRYING OUT THE INVENTION

EXAMPLE

The present invention is described in detail based on examples, however, the invention is not limited to the examples.

Active carbon fiber used in experiments or examples is the active carbon fiber from pitch (product of OSAKA GAS CHEMICAL CO., LTD.) having a specific surface area of 1,000 m²/g. A repellent used in experiments 1 to 4 is the repellent for birds in a mixture of four species of phenylethylalcohol, geraniol, citronellol and rosegeranium oil.

EXPERIMENT 1

A 0.5 g of active carbon fiber was dipped and impregnated with a mixture of 90 parts by weight of DEP (diethylphthalate) as a sustained release agent and 10 parts by weight of the repellent until saturated. After suspending the active carbon fiber taken out from the mixture and threaded for 1 hour at room temperature, the adsorbed material was weighed with a balance. The weight was defined as a initial weight. The active carbon fiber impregnated with the mixture was allowed to stand in a thermostat at 60° C. to accelerate release of adsorbed substances and measured changes of the weight (a value calculated by subtracting a weight of the fiber from the total weight, i.e., a residual quantity of adsorbed substances) of the fiber with time. The results of the measurement are shown as curve A in FIG. 1.

Figure 1:
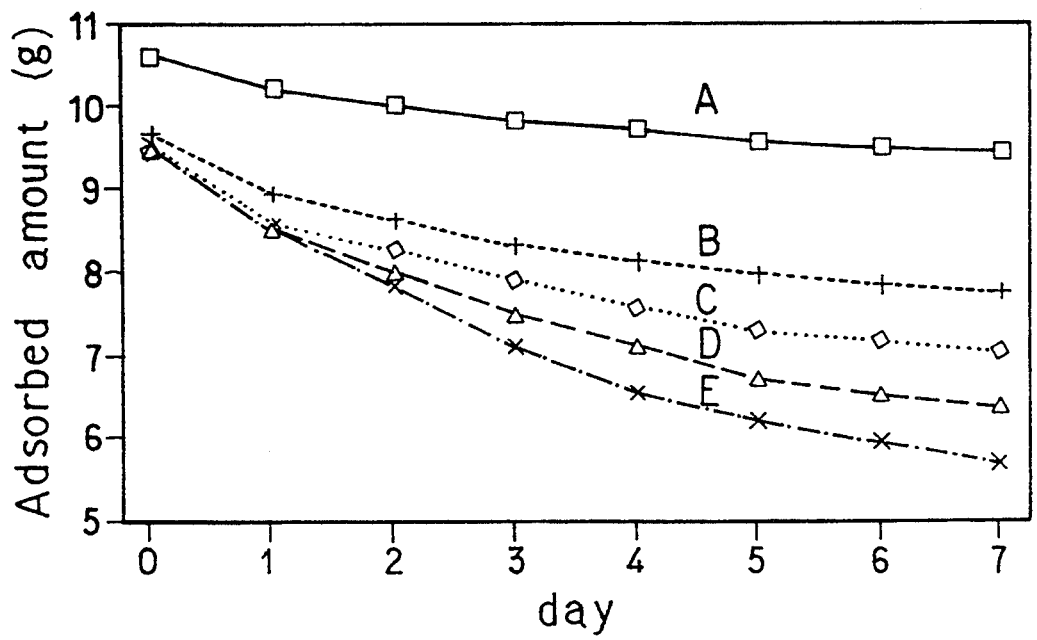
FIG. 1 indicates a result of determining a residual quantity of adsorbed material while changing an amount of DEP (diethylphthalate) used in conditions that the repelling material produced by impregnating a 0.5 g of active carbon fiber with a mixture of a repellent and DEP (diethylphthalate) until saturated is allowed to stand in a thermostat at 60° C.

FIG. 1 also disclose data described as B, C, D and E when changing the proportion of DEP and the repellent to 80:20, 70:30, 60:40 and 50:50 respectively.

It is clear that using smaller amount of DEP causes considerable reduction of weight of the repelling material and that a life of the repelling material for animals becomes shorter.

EXPERIMENT 2

A 0.5 g of active carbon fiber was dipped and impregnated with a mixture of 80 parts by weight of TEC (triethyl citrate) as a sustained release agent and 20 parts by weight of the repellent until saturated. After suspending the active carbon fiber taken out from the mixture and threaded for 1 hour at room temperature, the weight of adsorbed material (initial weight) was determined with a balance. The active carbon fiber impregnated with the mixture was allowed to stand in a thermostat at 60° C. and measured changes of the weight of the fiber. The results of the measurement are shown as curve F in FIG. 2.

Figure 2:
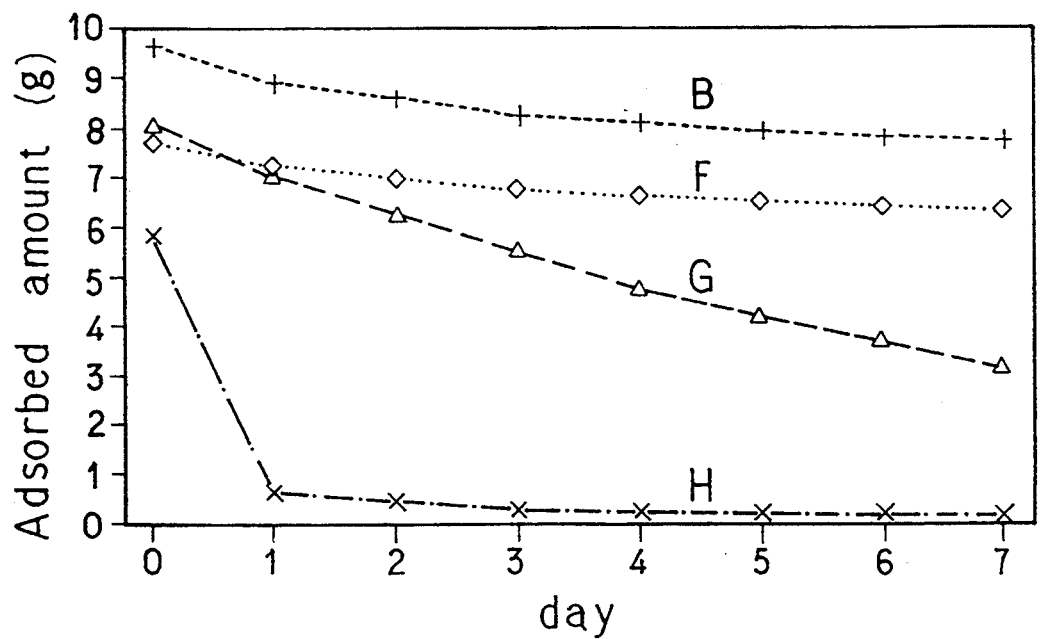
FIG. 2 indicates a result of determining a residual quantity of adsorbed material while changing a kind of a sustained release agent used in conditions that the repelling material produced by impregnating a 0.5 g of active carbon fiber with a mixture of a repellent and a sustained release agent until saturated is allowed to stand in a thermostat at 60° C.

FIG. 2 also discloses changes of weights as curves G and H when using DPG (dipropyleneglycol) and ethanol as a sustained release agent. The proportion of the repellent and the sustained release agent is 20:80 in all cases. In addition, data of experiment 1 that the proportion of the repellent and DEP (diethyl phthalate) is 20:80 are also shown as curve B.

It is clear that DEP, TEC and DPG has a sustained release effect in this sequence, and that ethanol can hardly be expected in a sustained release effect because most of adsorbed material was released in one day.

EXPERIMENT 3

Using commercially available granulated active carbon from coconut husk having a specific surface area of 480 m²/g as a carrier, a 0.5 g of granulated active carbon was dipped and impregnated with a mixture of 80 parts by weight of DEP as a sustained release agent and 20 parts by weight of the repellent until saturated. After suspending the granulated active carbon taken out from the mixture and threaded for 1 hour at room temperature, the weight of the adsorbed material (initial weight) was determined with a balance. The granulated active carbon impregnated with the mixture was allowed to stand in a thermostat at 60° C. and measured changes of the weight. The results of the measurement are shown as curve I in FIG. 3.

Figure 3:
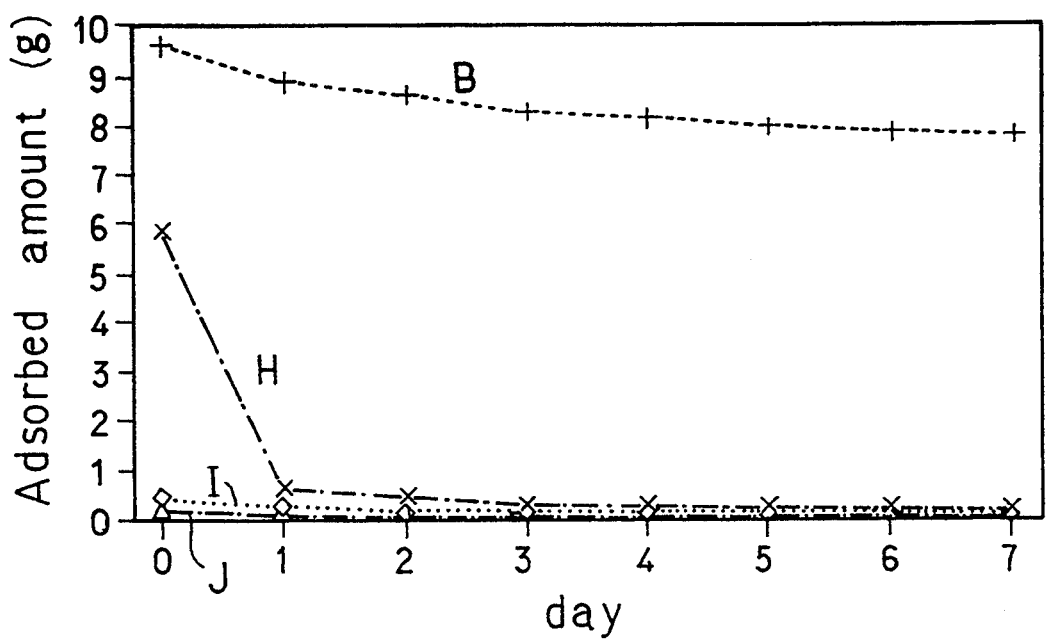
FIG. 3 indicates a result of determining a residual quantity of adsorbed material while changing a kind of a sustained release agent used in conditions that the repelling material produced by impregnating a 0.5 g of active carbon fiber or a 0.5 g of granulated active carbon with a mixture of a repellent and a sustained release agent until saturated is allowed to stand in a thermostat at 60° C.

FIG. 3 also discloses changes of weight described as curve J when using ethanol as a sustained release agent. The weight proportion of the repellent and the sustained release agent is 20:80. Additional data are shown as curve B when the proportion of a repellent and a sustained release agent, DEP, is 20:80 in experiment 1, further data are shown as curve H when the proportion of the repellent and sustained release agent, ethanol, is 20:80.

Although the specific surface area of granulated active carbon is 48% of the specific surface area of active carbon fiber, a retained quantity of the mixture of DEP and the repellent is only 3.4% of that of the active carbon fiber. Further, the active carbon fiber retained 89% of the initial weight after 7 days. In contrast, the granulated active carbon can retain adsorbed material as low as 28% of the initial weight.

The experiment clearly shows that using DEP as a sustained release agent with granulated active carbon hardly exerts a sustained release effect, and that using DEP as a sustained release agent with active carbon fiber exerts a considerable sustained release effect due to synergistic action with the active carbon fiber and DEP. This will be caused by that the active carbon fiber has different pore distributions and adsorption properties from those of granulated active carbon.

EXPERIMENT 4

To inspect an essential amount of the sustained release agent, an experiment was conducted without using any sustained release agent.

A 0.5 g of active carbon fiber was dipped in a solution consisting of only the repellent and impregnated with the solution until saturated. After suspending the active carbon fiber taken out from the solution and threaded for 1 hour at room temperature, the weight of the adsorbed material (initial weight) was determined with a balance. The active carbon fiber impregnated with the solution was allowed to stand in a thermostat at 60° C. and measured changes of the weight of the fiber. The results of the measurement are shown as curve Z in FIG. 4.

Figure 4:
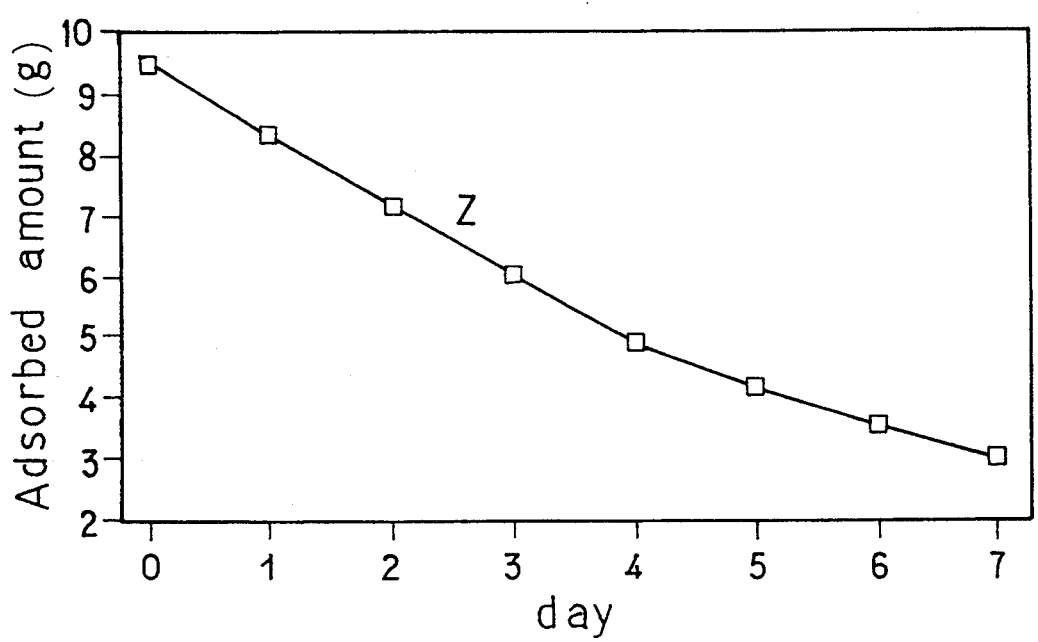
FIG. 4 indicates a result of determining a residual quantity of adsorbed material in conditions that the repellent produced by impregnating a 0.5 g of active carbon fiber with only a repellent until saturated is allowed to stand in a thermostat at 60° C.
Figure 5:
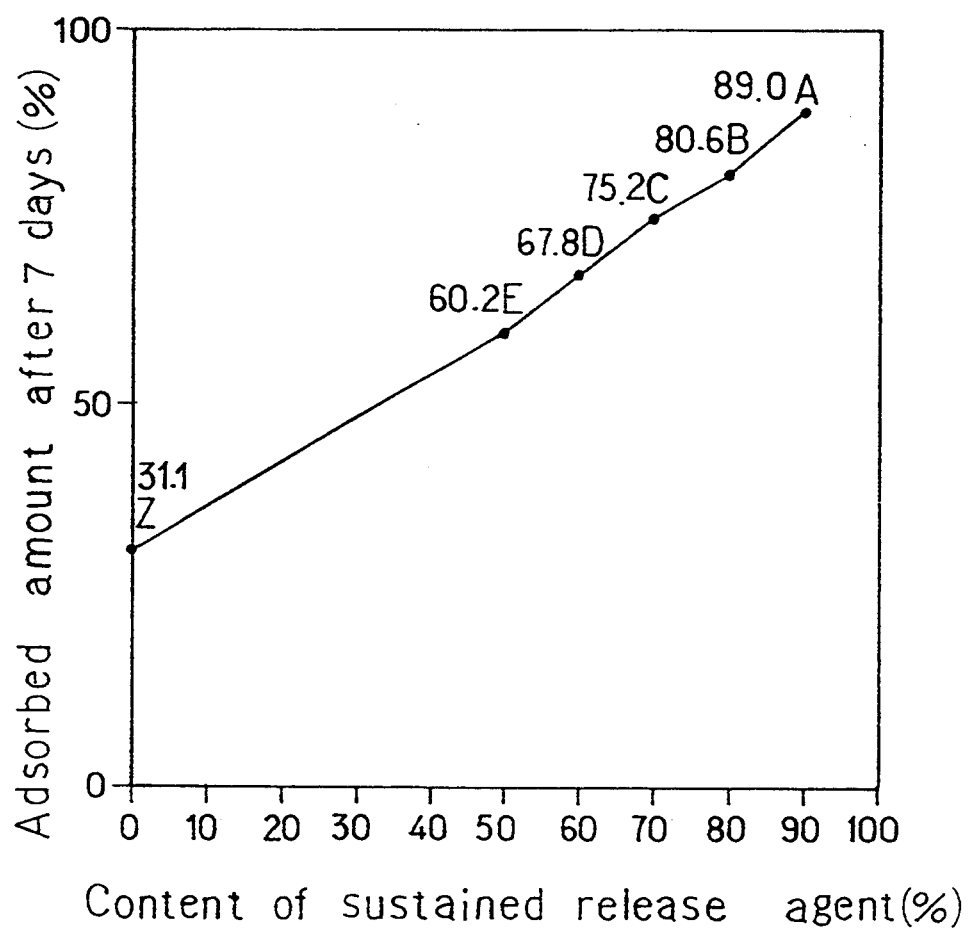
FIG. 5 indicates a result of determining a residual quantity of adsorbed material after 7 days while changing an amount of a sustained release agent, FIG. 6 indicates a result of determining a residual quantity of adsorbed material when a 1.0 g of active carbon fiber mixed unwoven fabric made of nylon and polyester and filter paper adsorbs a repellent and a sustained release agent until saturated.

FIG. 5 illustratively indicates a proportion of a residual quantity of adsorbed material on the repellent material corresponding to A, B, C, D and E in FIG. 1 after seven days and a residual quantity of adsorbed material on the repellent material corresponding to Z in FIG. 4 after seven days based on the initial weight of the adsorbed quantity respectively. FIG. 5 shows that 50 or more % (at least 1 part by weight of the sustained release agent per 1 part by weight of the repellent) of content of sustained release agent is necessary, if evaluation standard is determined whether a residual quantity is twice as much as the quantity of residue without using a sustained release agent.

EXPERIMENT 5

A 1 g of carriers are produced by using (1) active carbon fiber from pitch supported by unwoven fabric made of polyester in both sides (product of OSAKA GAS CHEMICAL CO., LTD., Commodity code: FN200PS10) having a weight per unit area of 200 g/m$^2$ and a specific surface area of 1,000 m$^2$/g, (2) mixed unwoven fabric made of nylon and polyester, and (3) filter paper respectively. After these carriers were dipped in a mixture of 20 parts by weight of the repellent for pegions produced by mixing 4 speices, phenyl ethylalcohol, geraniol, citronellol and rosegeranium oil, and 80 parts by weight of diethyl phthalate as a sustained release agent, the carriers being allowed to suspend for 1 hour at room temperature (15° C.), the adsorbed material being weighed. Each adsorbed amount of carriers is 12.57 g in active carbon fiber carrier from pitch, 4.24 g in unwoven fabric carrier made of polyester and 0.88 g in filter paper carrier.

Figure 6:
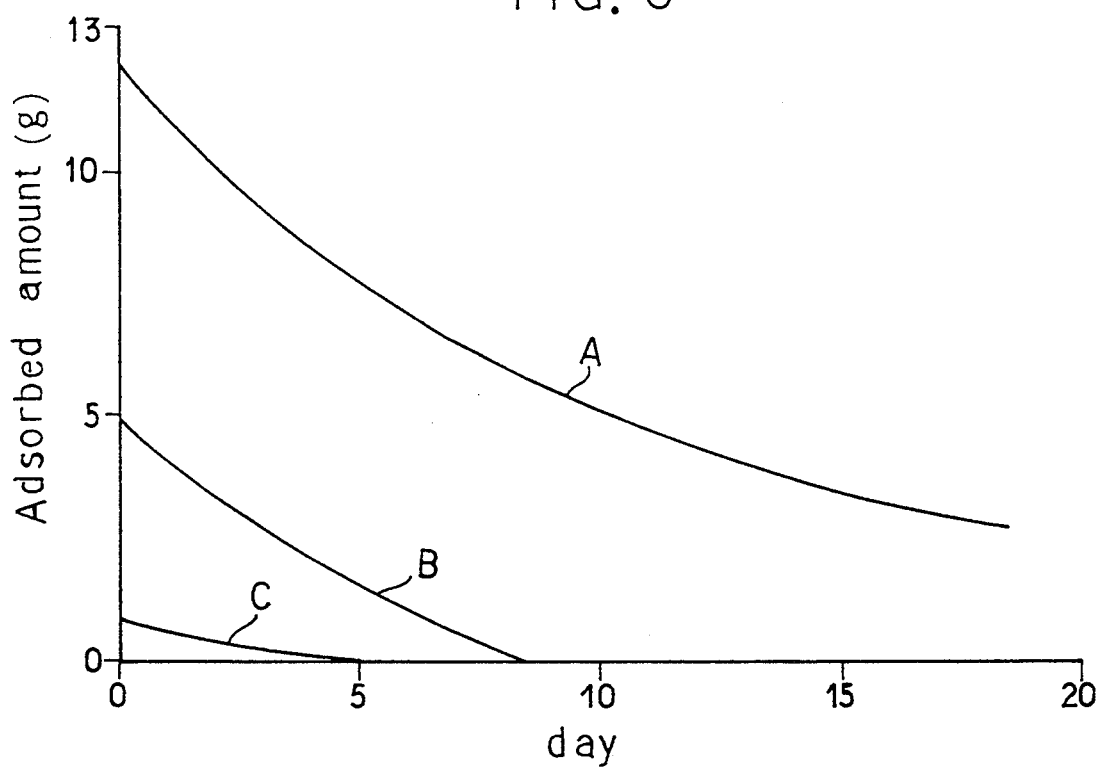

The samples were allowed to stand on a beaker in a thermostat at 60° C. and measured changes of the weight of the adsorbed material with time to obtain a graphic chart shown in FIG. 6.

Although the carrier from filter paper (shown as "C") and the carrier from mixed unwoven fabric made of nylon and polyester (shown as "B") lost all of repellent for birds by volatilization after 5 days and 8 days respectively, the carrier from unwoven fabric of active carbon fiber (shown as "A") still retained and adsorbed as much as about 3 g of the repellent for birds after 18 days.

It is clear that the active carbon fiber is better than mixed unwoven fabric made of nylon and polyester and filter paper in both adsorbed amount and a sustained release property as a carrier for a repelling material.

EXAMPLE 1

A solution for producing repelling material for birds were prepared by adding 80 parts by weight of diethylphthalate to 20 parts by weight of a repellent solution for birds containing about 58% of β-phenylethylalcohol, about 17% of citronellol, about 13% of benzylbenzoate, about 6% of geraniol, about 4% of linarylacetate and about 2% of lynalool.

Figure 7:
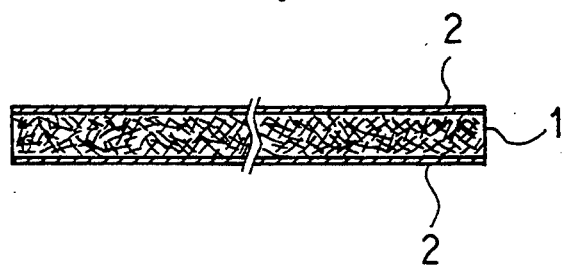
FIG. 7 indicates a sectional drawing of active carbon fiber supported by unwoven fabric made of polyester fiber.

Piled were two pieces of unwoven fabric of the active carbon fiber (product of OSAKA GAS CHEMICAL CO., LTD., Commodity Code: FN300PS) shown in FIG. 7 having a weight per unit area of about 300 g/m$^2$ (5 to 8 mm in thickness) as active carbon fiber obtained monolithically by conducting needle-punch after piled on both sides of active carbon fiber having a specific surface area of 1,000 g/m$^2$, and then about 4.3 mm×about 4.3 mm of a small piece (weight=1 g) of active carbon fiber was cut out, and a 10 g of the repellent solution for birds was added dropwise to the piece to adsorb the repellent.

After the obtained sample 3 was put in a container 4 made of metal having an inner diameter of 50 mm and a height of 27 mm, an inner lid 5 formed twelve opening 7 having a diameter of seven mm was put on the container, and the container was canned and sealed with can-forming device to produce a transferable can storing repellent material for birds.

After the sealed can storing the repellent for birds was allowed to stand for 1 month, the cover 6 was opened and the can was suspended at a tree where birds (pigeons, sparrows, bulbuls, etc) came flying in the park for 2 months to observe an effect of the repelling material. Birds (pegion, sparrow, bulbul, etc.) did not approach the tree suspending the can within a 10-meter radius from the tree, however birds came again flying around the tree after 3 weeks. This demonstrates that the present repellent is effective to avoid birds, in particular, pigeons, sparrows, bulbuls, etc.

EXAMPLE 2

Figure 8:
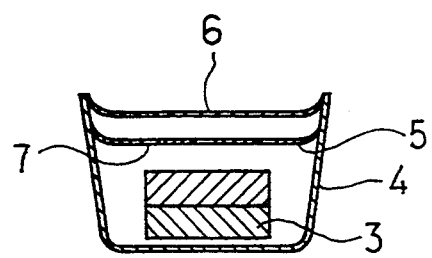
FIG. 8 shows repelling material for animals stored in a can.

A repellent solution was prepared by adding 80 parts by weight of diethyl phthalate to a 20 g of phenylethylalcohol. The solution was adsorbed on a 1 g of active carbon fiber in the same manner as in example 1, putting the fiber in the can shown in FIG. 8, sealing the can, opening the can after 1 month, and suspending the can at a tree in the park where birds (pigeons, sparrows, bulbuls, etc.) came flying. Birds did not become approaching the tree. However, birds become approaching the tree again after 3 weeks.

This demonstrates that DEP can be used to the repellent whose composition is different from that of example 1.

EXAMPLE 3

A repelling perfume for dogs and cats was prepared by mixing about 34 parts by weight of cinnamic aldehyde, about 6 parts by weight of γ-nonylolactone, about 57 parts by weight of limonene (major component of lemon oil) and 3 parts by weight of paracresolacetate, and a mixed solution of 20 parts by weight of this mixture and 80 parts by weight of diethylphthalate was prepared. To this mixture, the active carbon fiber used in experiment 5 was dipped, and the repellent for animal was adsorbed and retained on the active carbon fiber to give repellent material for dogs and cats.

This repelling material for animals was put near the garbage where cats often searched about for food to observe an effect of the repelling material.

Before placing the repellent, cats have gathered around the gabbage and brought down the gabbage to scatter about rubbish. However, after the repellent material was allowed to stand, cats did not approach the gabbage so that the place was kept clean., The effect continued for 3 weeks after placing the repelling material for animal.

Further, a 1 g of the active carbon fiber used in example 5 was dipped in a solution produced by dissolving 20 parts by weight of limonene in 80 parts by weight of diethylphthalate to give the repelling material for animals used for dogs and cats.

This repelling material for animals was put near the garbage where cats often searched about for food to observe an effect of the repelling material. An effect of the repelling material continued for 2 weeks. This assured that DPE is effective as a sustained release agent when the repellent is composed of only limonene.

INDUSTRIAL APPLICABILITY

When at least one substance of phthalic acid esters, citric acid esters and glycols was adsorbed and retained on active carbon fiber, a great amount of repellent can be adsorbed and retained, and also the repellent is gradually released to a high degree so that an excellent repelling material for animals being capable of using for a long time can be obtained.

We claim:

1. An article of manufacture comprising active carbon fiber impregnated with a repellant for animals and as a sustained release agent a substance selected from the group consisting of phthalic acid esters, citric acid esters and glycols.

2. The article of manufacture according to claim 1 wherein the phthalic acid esters are diethylphthalate or dibutylphthalate, the citric acid esters are "triethylcitrate or trimethylcitrate and the glycols are dipropyleneglycol or butyldiglycol.

3. The article of manufacture according to claim 1 wherein a total amount of phthalic acid esters, citric acid esters and glycols is in the range of 1 to 9 parts by weight per 1 part by weight of a repellent.

4. The article of manufacture according to claim 1 wherein the repellent is a repellent for birds.

* * * * *